US010912667B1

(12) United States Patent
Sickles et al.

(10) Patent No.: US 10,912,667 B1
(45) Date of Patent: Feb. 9, 2021

(54) ORTHOPEDIC BRACE

(71) Applicants: George Sickles, Louisville, KY (US); Steve Farmer, Louisville, KY (US)

(72) Inventors: George Sickles, Louisville, KY (US); Steve Farmer, Louisville, KY (US)

(*) Notice: Subject to any disclaimer, the term of this patent is extended or adjusted under 35 U.S.C. 154(b) by 314 days.

(21) Appl. No.: 15/880,891

(22) Filed: Jan. 26, 2018

Related U.S. Application Data

(60) Provisional application No. 62/451,133, filed on Jan. 27, 2017.

(51) Int. Cl.
| | | |
|---|---|---|
| *A61F 5/37* | (2006.01) | |
| *A61F 5/02* | (2006.01) | |
| *A61F 5/058* | (2006.01) | |
| *A61F 5/01* | (2006.01) | |

(52) U.S. Cl.
CPC .............. *A61F 5/3753* (2013.01); *A61F 5/02* (2013.01); *A61F 5/05858* (2013.01); *A61F 5/373* (2013.01); *A61F 2005/0167* (2013.01)

(58) Field of Classification Search
CPC .... A61F 5/3753; A61F 5/373; A61F 5/05858; A61F 5/02; A61F 2005/0167; A61F 5/3738; A61F 5/3723; B43L 15/00; F41C 27/22; A47B 2021/0392; Y10T 403/293; Y10T 403/299; Y10T 403/29; Y10T 403/291; Y10T 403/295; Y10T 403/297; F16B 7/06
USPC ............................ 248/118; 42/94; 403/43–48
See application file for complete search history.

(56) References Cited

U.S. PATENT DOCUMENTS

| | | | |
|---|---|---|---|
| 1,257,297 A | | 2/1918 | Brown |
| 1,639,815 A | * | 8/1927 | Siebrandt ............ A61F 5/05858 602/16 |
| 3,631,542 A | | 1/1972 | Potter |
| 4,651,719 A | * | 3/1987 | Funk ........................ A61F 5/013 482/901 |
| 4,913,393 A | * | 4/1990 | Wood ........................ A61G 5/10 224/407 |
| 5,033,461 A | * | 7/1991 | Young ................... A61F 5/3753 602/16 |
| 5,060,638 A | | 10/1991 | Bodine, Jr. |
| 5,329,941 A | | 7/1994 | Bodine, Jr. |
| 5,385,536 A | * | 1/1995 | Burkhead ............. A61F 5/3753 2/45 |
| 5,665,058 A | * | 9/1997 | Young ................... A61F 5/3753 602/16 |
| 6,554,234 B2 | * | 4/2003 | Holdren ................. B43L 15/00 248/118.5 |
| 6,659,971 B2 | | 12/2003 | Gaylord |
| 6,932,781 B2 | | 8/2005 | Itoi |
| D514,224 S | | 1/2006 | Fried |

(Continued)

OTHER PUBLICATIONS

U.S. Appl. No. 62/451,133 entitled "Orthopedic Brace" filed Jan. 27, 2017.

*Primary Examiner* — Rachael E Bredefeld
*Assistant Examiner* — Camtu T Nguyen
(74) *Attorney, Agent, or Firm* — Middleton Reutlinger

(57) ABSTRACT

The present embodiments provide a brace which includes an actuator. The actuator provides movement of the arm and shoulder, abduction movement, so that during recovery from shoulder surgery, the shoulder and arm movement may be supported in increased range of motion positions. This may be done with a single brace rather than requiring multiple braces during the recovery process.

7 Claims, 10 Drawing Sheets

(56) References Cited

U.S. PATENT DOCUMENTS

| | | |
|---|---|---|
| 7,189,213 B1 | 3/2007 | Weber |
| 7,244,239 B2 | 7/2007 | Howard |
| 7,300,410 B1 | 11/2007 | Weber |
| D561,902 S | 2/2008 | Fried |
| 8,016,780 B1 | 9/2011 | Sickles |
| 2005/0010147 A1 | 1/2005 | Kazmierezak et al. |
| 2008/0228116 A1 | 9/2008 | Walker |

* cited by examiner

ORTHOPEDIC BRACE

CLAIM TO PRIORITY

This non-provisional patent application claims priority to and benefit of, under 35 U.S.C. § 119(e), U.S. Provisional Patent Application Ser. No. 62/451,133, filed Jan. 27, 2017 and titled "Orthopedic Brace", all of which is incorporated by reference herein.

BACKGROUND

1. Field of the Invention

Present embodiments relate to an orthopedic brace which aids in recovery from shoulder surgery as well as pre-operative therapy. More specifically, present embodiments relate to the orthopedic brace and an actuator used with the brace to increase abduction range of motion of the shoulder before or after surgery.

2. Description of the Related Art

Shoulder abduction complications are common after shoulder surgery, particularly with rotator cuff repairs. The rotator cuff muscles stabilize the shoulder joint, keeping the ball of the arm bone in the joint socket as the arm moves. Of the tendons associated with the rotator cuff muscles, the supraspinatus tendon is most commonly injured. This muscle performs shoulder abduction, arm movement out to the side and away from the body.

Following shoulder surgery, it is desirable to force a patient's arm and shoulder to move from a position close to the body to a second position further from the body. This is commonly referred to as abduction movement and increasing this movement during the recovery is desirable along with physical therapy. Thus, increasing the user's range of motion.

Current braces support the arm generally in a fixed position. For example, a sling may be used and a pad may be inserted between the arm and body. This moves the arm away from the patient's body. The distance may be varied by changing the size of pad, the arm may therefore be moved toward or away from the body. However, prior art braces fail to provide easy adjustability to increase abduction of the arm, with a single brace.

It would be desirable to provide a shoulder brace of minimal complication which may be easily adjusted to increase range of motion of the shoulder and upper arm during recovery, which may be either pre-operative or post-operative and independent of surgery.

The information included in this Background section of the specification, including any references cited herein and any description or discussion thereof, is included for technical reference purposes only and is not to be regarded subject matter by which the scope of the invention is to be bound.

SUMMARY

The present application discloses one or more of the features recited in the appended claims and/or the following features which alone or in any combination, may comprise patentable subject matter.

The present embodiments provide a brace which includes an actuator. The actuator provides movement of the arm and shoulder, abduction movement, so that during recovery from shoulder surgery, the shoulder and arm movement may be supported in increased range of motion positions. This may be done with a single brace rather than requiring multiple braces during the recovery process.

According to some embodiments, an actuator for an orthopedic brace comprises a first threaded body having a platform end defining at least a portion of a connector, a second threaded body which receives the first threaded body, a rotating grab connected to one of the first threaded rod and the second threaded body, the grab providing rotation of one of the first threaded body and the second threaded body to the other, a third threaded body which engages the second threaded body, wherein rotation of the grab also provides rotation of the second threaded body to the third threaded body.

Optionally, the following embodiments may be used with the actuator, either alone or in any of various combinations. The first threaded body may be a rod. The actuator may further comprise a hollow sleeve defined within the first threaded body. The actuator may further comprising a cap engaging the third threaded body, the cap having a guide rod which extends into the hollow sleeve. The second threaded body may be threaded internally and externally. The second threaded body may further comprise a hollow threaded interior which receives the first threaded body. The third threaded body may be a threaded sleeve. The first connector and a second connector may each have at least one of a clevis and a tang. The first threaded body may be threaded in a first direction. The second threaded body may have a first internal thread configured to operate with the first threaded body. The actuator second threaded body having a second external thread which is threaded in a second direction. The third threaded body may be threaded and configured to operate with the second external thread. The actuator may further comprise an extension which may be connected to the actuator to lengthen the actuator.

According to some embodiments, an orthopedic brace comprises a body brace and an arm platform, an actuator which is movable to extend and retract the arm platform relative to the body brace, the actuator comprising a first threaded body, a second threaded body and a third threaded body, a first end of the actuator having a connector which engages the arm platform, the connector providing angular adjustment of the actuator relative to the arm platform, a second end of the actuator having a second connector which engages the body brace.

Optionally, the following embodiments may be used with the actuator, either alone or in any of various combinations. The first threaded body may have a thread in a first direction. The second threaded body may having a first thread in the first direction and a second thread in a second direction. The third threaded body having a third thread in the second direction. The orthopedic brace may further comprising a guide rod extending from one side of the actuator to a second side to inhibit rotation of at least one of the body portion and the arm platform. The second connector may provide angular adjustment as the actuator relative to the body brace. The orthopedic brace may further comprising an extension which may be connected to the actuator.

According to some embodiments an actuator of an orthopedic brace, comprises a first body which extends and retracts relative to a second body, a third body which extends and retracts relative to the second body, a body brace at one end of the actuator, an arm platform at a second end of the actuator; at least one of the body brace or the arm platform being angularly adjustable relative to the actuator. Optionally, the actuator may further comprise an extension to lengthen the actuator.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. All of the above outlined features are to be understood as exemplary only and many more features and objectives of the various embodiments may be gleaned from the disclosure herein. Therefore, no limiting interpretation of this summary is to be understood without further reading of the entire specification, claims and drawings, included herewith. A more extensive presentation of features, details, utilities, and advantages of the present invention is provided in the following written description of various embodiments of the invention, illustrated in the accompanying drawings, and defined in the appended claims.

BRIEF DESCRIPTION OF THE DRAWINGS

In order that the embodiments may be better understood, embodiments of an orthopedic brace will now be described by way of examples. These embodiments are not to limit the scope of the claims as other embodiments of an orthopedic brace will become apparent to one having ordinary skill in the art upon reading the instant description. Non-limiting examples of the present embodiments are shown in figures wherein:

DETAILED DESCRIPTION

Figure 1:
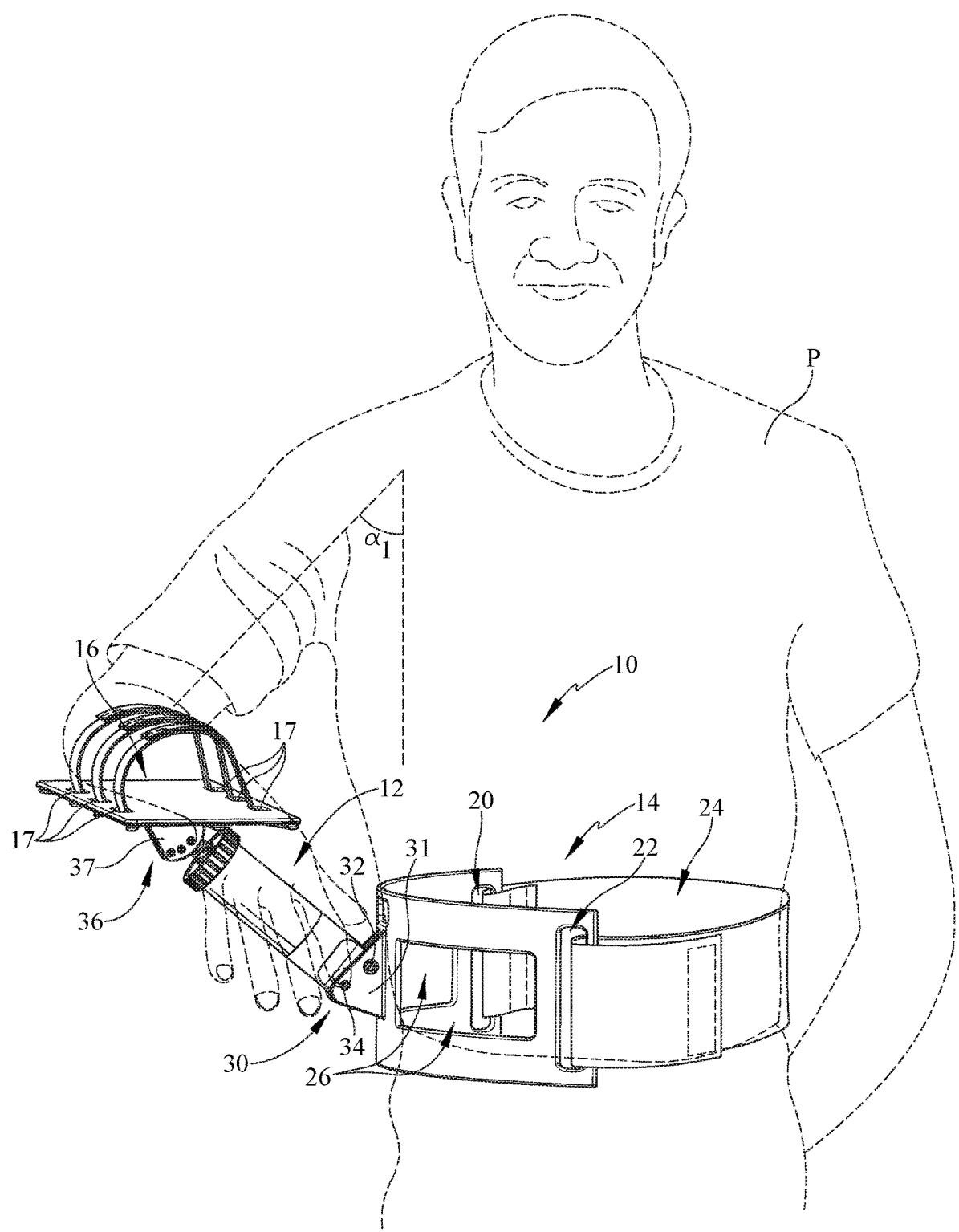
FIG. 1 is a perspective view of an embodiment of a patient using an orthopedic brace with an actuator in a first position so that the arm is closer to the patient's body.

It is to be understood that an orthopedic brace is not limited in its application to the details of construction and the arrangement of components set forth in the following description or illustrated in the drawings. The described embodiments are capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

Referring now to FIGS. 1-10, the instant orthopedic brace provides for improved abduction movement and support of an arm and shoulder either before or after surgery, and during a recovery process. The orthopedic brace may be adjusted from a more retracted position to an extended position so that an arm may be moved from near the body immediately following surgery to away from the body as the shoulder recovers and range of motion increases. As the range of motion increases, the arm is supported by the brace in the positions further from the body, allowing the shoulder tissue to stretch and thus improve the range of motion.

Referring now to FIG. 1, a perspective view of an orthopedic brace 10 is shown for use with a patient P, for example following shoulder surgery. The orthopedic brace 10 comprises an actuator 12 which is movable between a retracted position shown in FIG. 1 and an extended position shown in FIG. 2.

The orthopedic brace 10 also comprises a body brace 14 at one end of the actuator 12 and an arm platform 16 at an opposite end of the actuator 12. The body brace 14 is formed to engage the patient's body to provide a foundation or brace against which the actuator 12 may support and move the platform 16. The body brace 14 may be formed of various materials including plastics which may be rigid or bendable to better conform to the patient's body shape.

In the depicted embodiments, the brace 14 is generally rectangular and curved to fit around a user's body. The body brace 14 may comprise first and second strap apertures 20, 22. A strap or belt 24 is shown passing through the apertures 20, 22 and around the patient's body. The strap 24 may be tightened so that the body brace 14 is securely fitted against the patient's body. The strap 24 may be any of polyester, vinyl, cotton, leather or other known materials or combinations which may be securely fitted to the body brace 14 and to use the patient's body. Further, the strap 24 may include hook and loop structures so that the strap 24 may be tightened easily or removed easily by the patient. The strap 24 may be a single structure or may be formed of multiple strap structures which are joined together by any various types of fasteners, including but not limited to, the hook and loop type described, buttons, buckles or the like.

Further, the body brace 14 shown with weight saving reliefs 26. These reliefs 26 may be various shapes and/or numbers while providing some weight savings for the body brace 14. Likewise, the reliefs 26 may improve the bending of the body brace 14, for improved fitting of the body brace 14. Any reliefs however should not jeopardize the structural integrity of the body brace 14.

Also shown extending from the body brace 14 is a connector 30. It may be desirable that the body brace 14 may be adjusted at various angles relative to the actuator 12 or vice-versa. The connector 30 provides angular adjustment of the actuator 12 relative to the body brace 14 to provide improved adjustability of the orthopedic brace 10. The instant connector 30 is defined by a bracket 31, a pivot 32 and at least one retainer 34 at an end of the actuator 12. The pivot 32 allows movement of the brace 14 relative to the actuator 12 or vice versa. The retainer 34 may be defined by a hole which aligns with a hole in the actuator 12 and retains the position of the actuator 12 relative to the body brace 14, or vice versa. A pin 64 (FIG. 3) may be positioned through the connector 30 to retain the actuator 12 at the desired position. While one retainer 34 is shown, multiple holes may be used to improve angular adjustment. Alternatively, one of the actuator 12 and connector bracket 31 may have at least one male part and the other of the bracket 31 and actuator 12 may have a female part which engages at preselected positions. For example, a spring biased male structure may be used to adjust position relative to a female structure.

Similarly, the opposite end of the actuator 12 comprises a connector 36 which allows for adjustment of the platform 16 relative to the actuator 12 or vice versa. The connector 36 may be formed of a bracket 37 at an end of actuator 12. The bracket 37 may also comprise a pivot and a retainer to fix the actuator 12 at a desired angle relative to the platform 16.

The platform 16 is depicted as a flat structure with a plurality of holes 17 to receive one or more straps. The straps retain the arm on the platform 16. In other embodiments, the platform 16 may be curved to approximate curvature of a patient's arm.

Also shown on FIG. 1 is an angular representation related to the patient's arm and shoulder. A vertical broken line is depicted for reference and a second line at some angle $\alpha_1$, relative to the vertical line represents angle of the upper arm from the reference line. As compared with FIG. 2, the arm position is changed with extension of the actuator 12. The angle $\alpha_2$ represents the actuator 12 in an extended position as opposed to the retracted position in FIG. 1.

Figure 2:
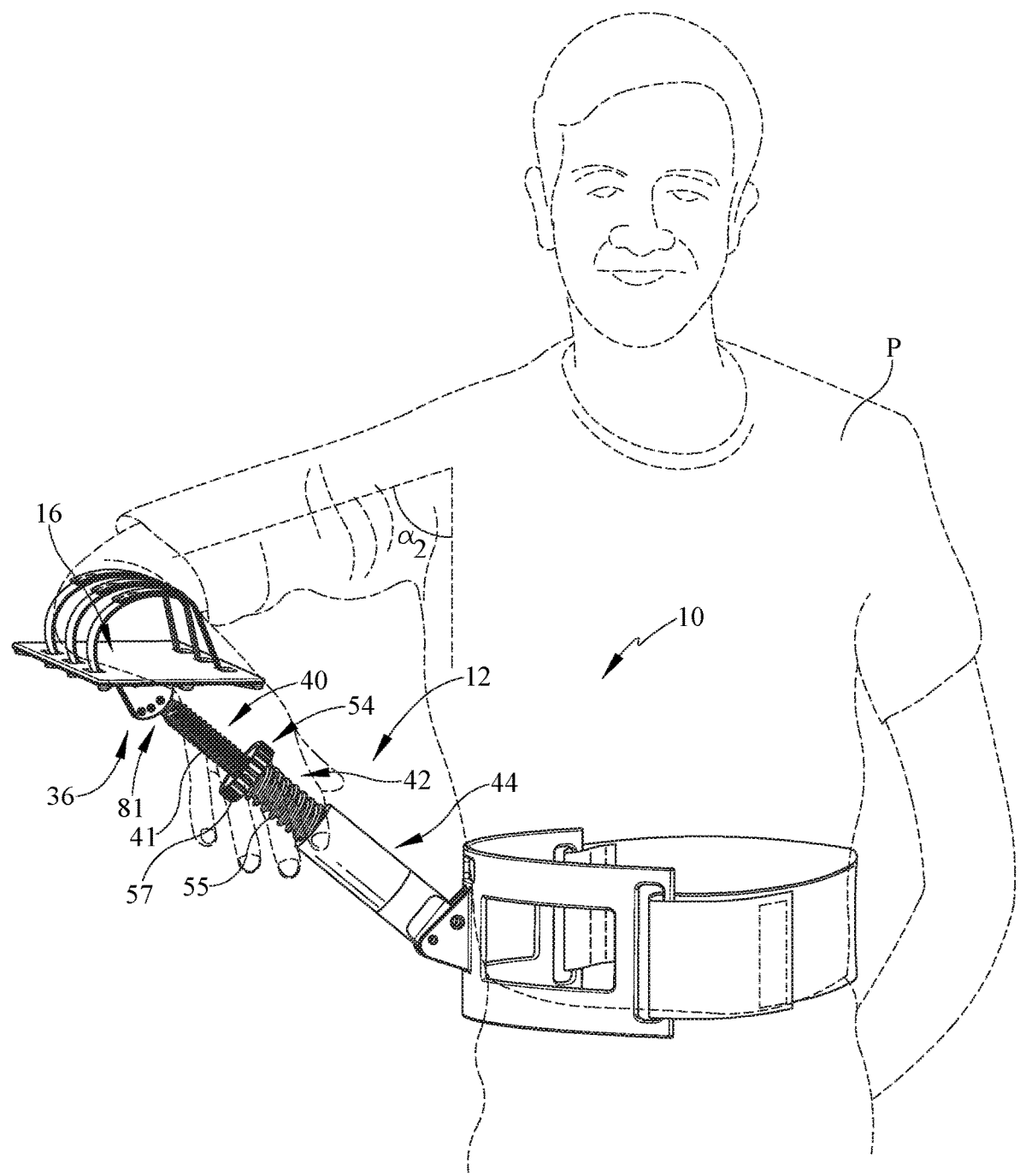
FIG. 2 is a perspective view of the patient and the orthopedic brace with the actuator in a second position so that the arm is further from the patient's body.

Referring now to FIG. 2, a perspective view of the orthotic brace 10 is depicted. In this view, the actuator 12 is shown in a more extended configuration which corresponds to the patient's arm being in a more abducted position and rotated away from the body. The actuator 12 comprises a first threaded body 40, a second threaded body 42 and a third threaded body 44. The threaded bodies 40, 42, 44 work together to provide the extension and retraction of the actuator 12. As the actuator 12 extends, the shoulder is forced to stretch with movement of the arm away from the body and increase the range of motion while the retraction allows for downward movement of the shoulder and arm closer to the body. The actuator 12 may be used to aid in stretching movement of the arm/shoulder joint or may merely be used for support of the arm at some position.

Figure 4:
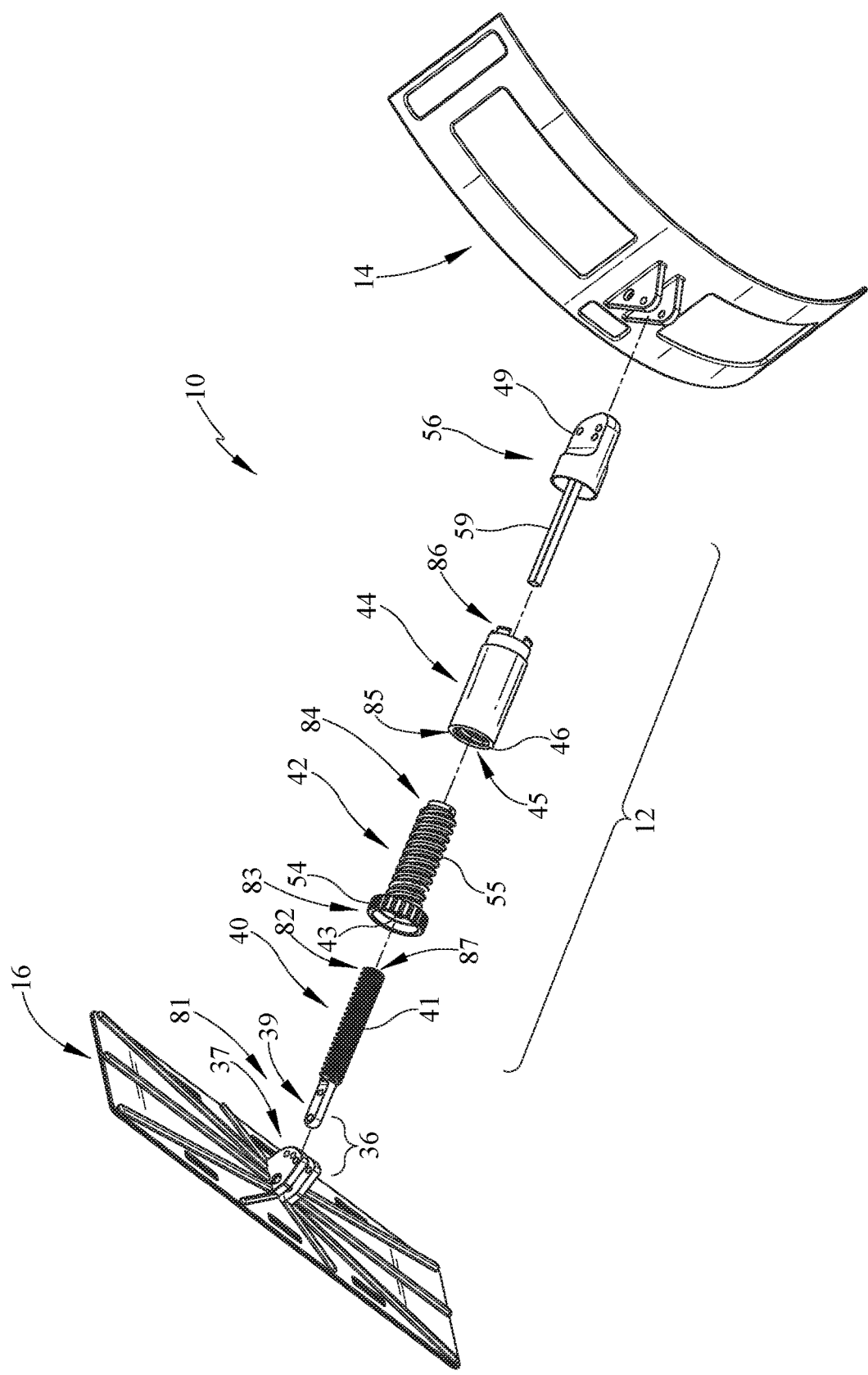
FIG. 4 is an exploded perspective view of the brace and actuator.

At the upper end of the brace 10, the first threaded by 40 connects to the platform 16. The connector 36 is defined between the platform 16 and the first threaded body 40. The first threaded body 40 may be a rod-like structure with one or more external threads 41. The one or more threads 41 may be continuous or may be segments. The threads 41 may have various pitch, angle, and threads per inch, all of which may affect operation. The first threaded body 40 comprises a first end 81 and a second end 82 (FIG. 4). The first end 81 defines a portion of the connector 36 while the second end 82 extends into the second threaded body 42.

The one or more external threads 41 extend into the second threaded body 42 to provide guided movement into and out of the second threaded body 42. Additionally, as may be discerned from the drawings, the one or more threads 41 are shown turning about the first threaded body 40 in a first direction. As will be described further herein, this direction is opposite the external threads 55 of the second threaded body 42. The rotation results in linear motion (extension/retraction) of the actuator 12.

The second threaded body 42 is also shown defining the actuator 12. The second threaded body 42 includes a grab 54 which allows rotation of the second threaded body 42 relative to the first threaded body 40. As one of skill in the art can realize, the first end 81 of first body 40 is fixed and similarly, the third threaded body 44 is fixed precluding rotation. Thus, the second threaded body 42 rotates creating linear motion of the actuator 12. The second threaded body 42 comprises one or more threads 55 which extend into the third threaded body 44. The second threaded body 42 may therefore be rotated into or out of the third threaded body 44. The grab 54 allows rotational input to the second threaded body 42 to allow such movement relative to the third threaded body 44.

Further, the one or more threads 55 may be opposite thread direction of the one or more threads 41 of the first threaded body 40. With this design, rotation of the grab 54, in a first direction, may cause one of extension and retraction of both the first threaded body 40 and the second threaded body 42 while rotation of the grab 54 in a second direction may cause the other of extension and retraction of the first threaded body 40 and the second threaded body 42.

As depicted, the grab 54 may be round and may have a plurality of gripping elements 57 or alternatively some knurled or other friction increasing surface texture. The grab 54 allows for rotational input to the second threaded body 42 thus moving the second threaded body 42 relative to the third threaded body 44 as well as the first threaded body 40 relative to the second threaded body 42.

Figure 3:
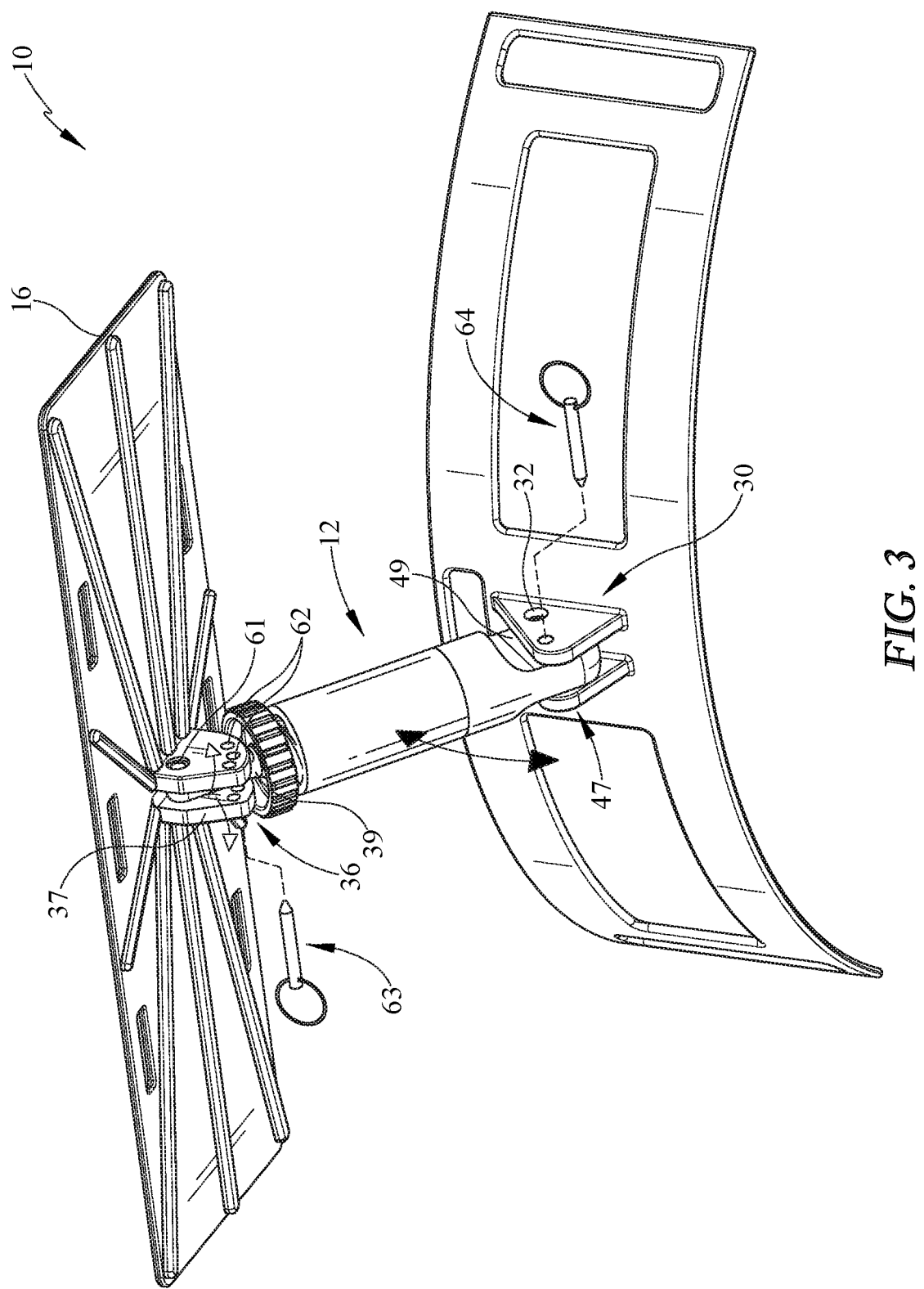
FIG. 3 is a lower perspective view of the brace removed from the patient and in the first position.

Referring now to FIG. 3, a lower perspective view of the orthopedic brace 10 is depicted. In this view, additional adjustment capabilities are more clearly shown. At the upper end of the brace 10, a connector 36 is shown at a lower surface of the platform 16. The connector 36 is generally formed by a clevis 37 and a tang 39. Other structures may be utilized to provide adjustability, however the connector 36 provides angular adjustment of the platform 16 relative to the actuator 12. The clevis 37 may be one type of bracket, previously described, and the tang 39 allows for angular adjustment relative to the clevis 37, as well as retention. Thus the platform 16 may be adjusted to different angles which may occur for various reasons including, but not limited to, body shape and size. The clevis 37 includes a pivot 61 and a plurality of adjustment apertures 62. The pivot 61 provides for the rotation of the actuator 12 relative to the platform 16. The aperture 62 receives a pin 63 to lock the actuator 12 in a position relative to the platform 16. More specifically, the tang 39 receives the pin 63 through the aperture 62 to lock the tang 39 in a position relative to the clevis 37.

Likewise, at the lower end of the actuator 12, a pivot 32 is defined as part of the connector 30. The connector 30 may be defined by a clevis 47 and tang 49. The clevis 47 may be one type of the previously described bracket 31. However, various structures may be utilized. Further, a pin 64 may be utilized relative to lock the actuator 12 or body brace 14 in a desired position. Two double headed arrows are provided to show adjustment of actuator 12 and the platform 16.

Referring now to FIG. 4, an exploded perspective view of the orthopedic brace 10 is depicted. In this view, the platform 16 is shown at the left-hand side of the figure, and the body brace 14 is shown at the right-hand side of the figure. Between the platform 16 and the body brace 14 is the actuator 12, which is exploded.

Starting with the first threaded body 40, the tang 39 is shown exploded from the clevis 37, together which form the connector 36. The first threaded body 40 may have a rod-like shape with at least one thread 41 disposed thereon. The at least one thread 41 is received by the second threaded body 42 so that the first threaded body 40 may move into or out of the second rib body 42. The first threaded body 40 may also have an internal sleeve which receives a guide rod 59, described further herein.

In order to accommodate receipt of the first threaded body 40, the second threaded body 42 has a hollow interior with at least one thread 43 which corresponds to the at least one thread 41. The threads 43 allow linear movement of the first threaded body 40 relative to the second threaded body 42 by way of rotational input.

The second threaded body 42 has a first end 83, a second end 84 and also comprises the external thread 55. The second threaded body 42 is also formed to move into and out of the third threaded body 44. The third threaded body 44 has a hollow interior 45 which includes at least one thread 46. The at least one thread 46 corresponds to the at least one thread 55 so that the second threaded body 42 may move linearly in a guided fashion relative to the third threaded body 44 with rotational input. When the grab 54 is rotated, the second threaded body 42 may move into the third thread body 44 and simultaneously the first threaded body 40 moves into the second threaded body 42. Alternatively, if the grab 54 is rotated in the opposite direction, the second threaded body 42 moves out of the third threaded body 44 and the first threaded body 40 moves out of the second threaded body 42.

Next to the second threaded body 42 is the third threaded body 44 which includes the hollow interior 45 and at least one thread 46 therein. The at least one thread is 46 allows for threaded engagement of the at least one thread 55 of the second threaded embodiment. This provides guided linear movement of the second threaded body 42 relative to the third threaded body 44.

The third threaded body 44 is generally cylindrical in shape and hollow providing space for the second threaded body 42 to move therein. The threaded body 44 includes a first end 85 and a second end 86, wherein the second end is engaged by a cap 56. The cap 56 may be formed integrally with the body 44 or connected during manufacturing.

The cap 56 encloses the actuator 12 and includes the tang 49 to provide angular adjustment with the body brace 14. The cap 56 also includes an anti-rotation or guide rod 59 which extends through the third threaded body 44, the second threaded body 42, and through an aperture in the first threaded body 40. The anti-rotation rod 59 inhibits rotation of the body brace 14 relative to the actuator 12. Further, by limiting the relative motion of the body brace 14 and the platform 16, the extension and retraction motion may be controlled by the grab 54 on the second threaded body 42. Likewise, since the cap 56 is connected to the body brace 14 and platform 16 is connected to first threaded body 40, the first and third bodies 40, 44 cannot rotate. Movement of these structures is limited to linear movement, created by rotation of the second threaded body 42.

Figure 5:
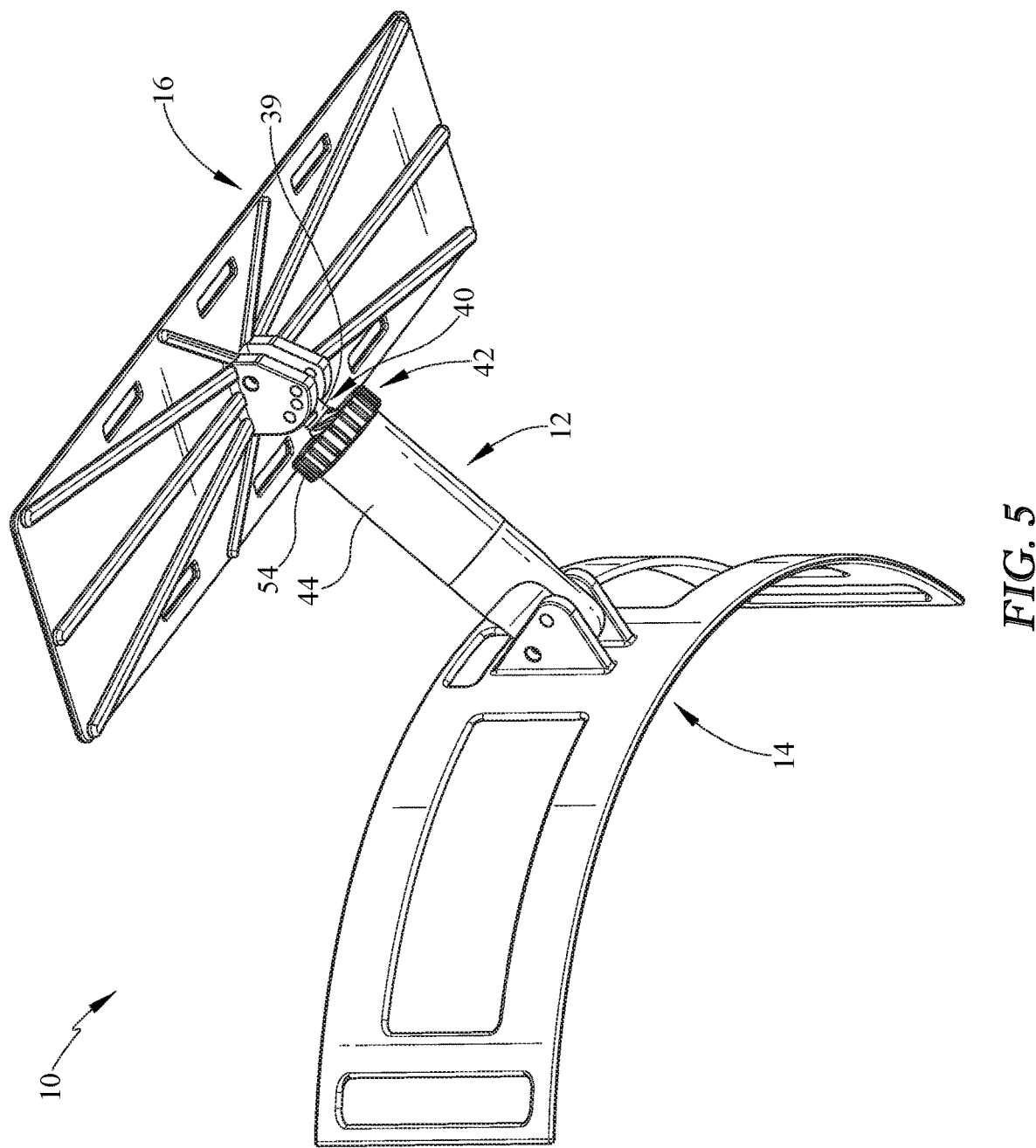
FIG. 5 is a first sequence perspective view showing the actuator in retracted position.
Figure 6:
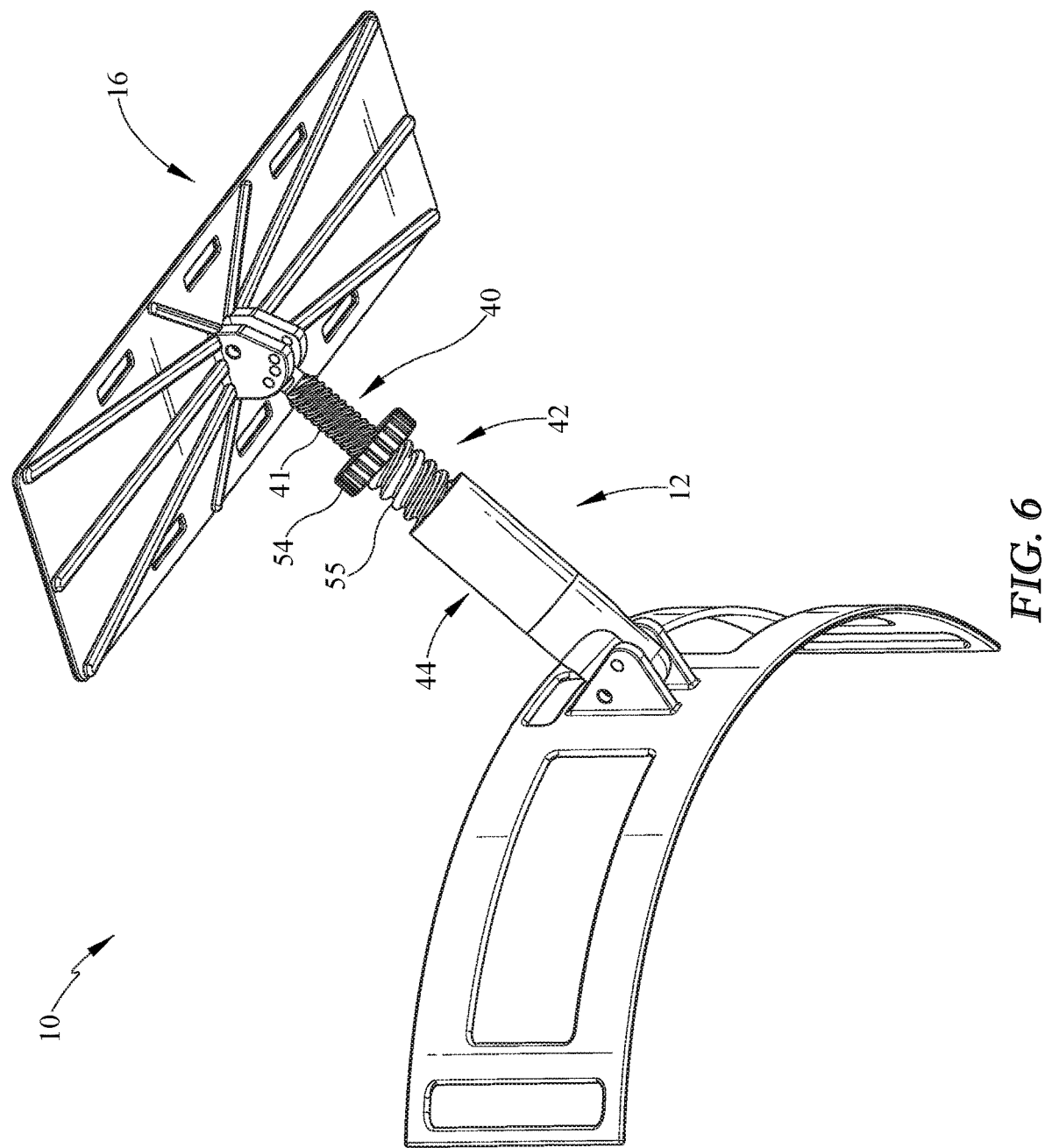
FIG. 6 is a second sequence perspective view showing the actuator in partially extended position.
Figure 7:
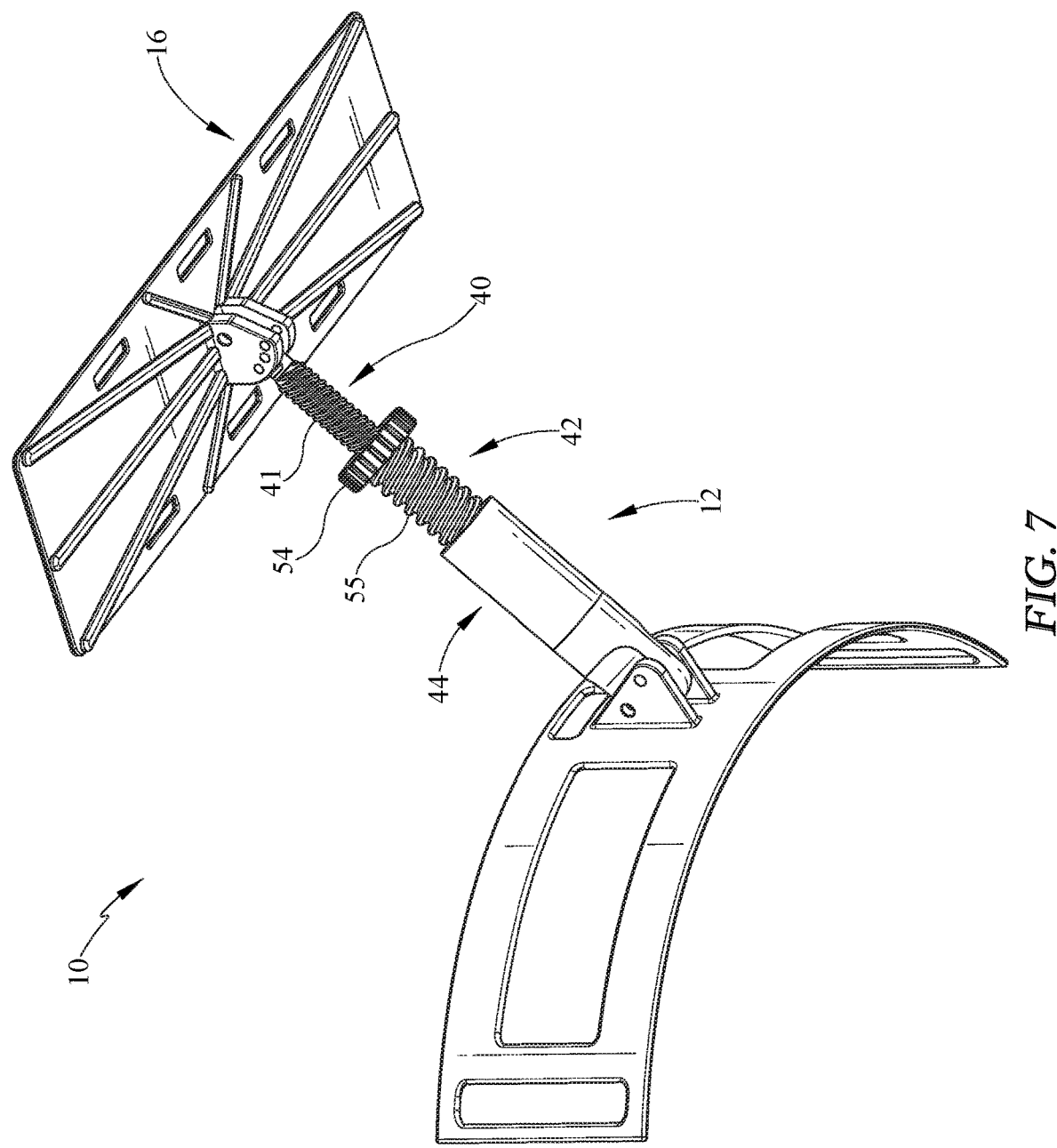
FIG. 7 is a third sequence perspective view showing the actuator in more fully extended position.

Referring now to FIGS. 5-7, a series of sequenced perspective views are shown depicting the operation of the actuator 12. With reference to FIG. 5, the actuator 12 is shown in a retracted position between the body brace 14 and the platform 16. Specifically, the threaded body 40 is disposed within the second body 42 so that generally only the tang 39 of the first threaded body 40 may be seen. Similarly, the second threaded body 42 is generally fully retracted into the third threaded body 44, so that the grab 54 is only visible at the end of the third body 44. From this position, the actuator 12 may be moved by rotating the grab 54 some amount to cause extension of the first threaded body 40 and the second threaded body 42.

With reference now to FIG. 6, the actuator 12 is again shown with the brace 10 and the actuator 12 is moved to a second position, which is partially extended from the position shown in FIG. 5. In this depiction, the grab 54 has been rotated from the position shown. As such, the first threaded body 40 is extended from the second threaded body 42, as depicted by the length shown of the at least one thread 41. Further, the second threaded body 42 is also shown extending from the third threaded body 44. This is depicted by the at least one thread 55 extending from the third threaded body 44 and the grab 54 which is spaced from the third threaded body 44.

Still further, with reference now to FIG. 7, the actuator 12 is shown in a fully extended position relative to FIGS. 5 and 6. Again, the length of the thread 41 shown is increased as opposed to that of FIG. 6. Likewise, the at least one thread 55 is also extended a further length from the third threaded body 44 as compared to FIG. 6. The actuator 12 may include internal or external stops to prevent over extension or retraction of the bodies 40, 42, 44. The movement is again provided by rotation of grab 54.

Figure 8:
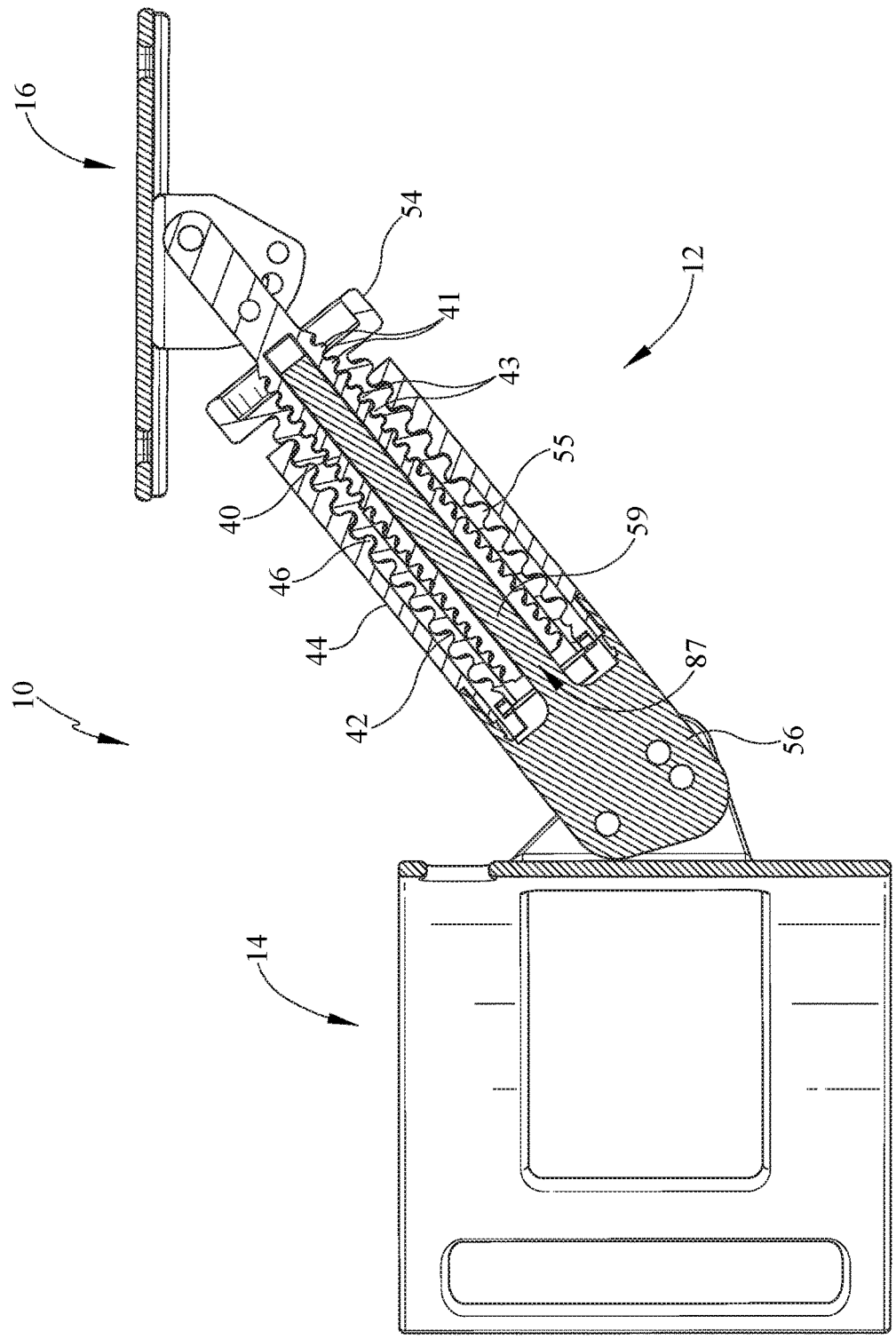
FIG. 8 is a section view of the actuator in the first more retracted position.

With reference now to FIG. 8, a section view of the actuator 12 is shown. The actuator 12 may include a plurality of threads as previously described and the instant figure shows the engagement of the threads to provide movement. In the depicted view, the cap 56 is shown at an end of the actuator 12, specifically third threaded body 44, to engage with the body brace 14, while the platform 16 is shown at the opposite end of the actuator 12.

The third threaded body 44 includes the at least one thread 46 which is shown engaging the external threads 55 of the second threaded body 42. This engagement provides for guided linear movement of the second threaded body 42 relative to the third threaded body 44 with rotation of the grab 54.

In this view, the second threaded body 42 is also shown with at least one thread 43 which engages the first threaded body 40 and specifically, the threads 41 thereof. With rotation of the grab 54, the first threaded body 40 also moves relative to the second threaded body 42.

It should be clear to one skilled in the art that rotation of the grab 54 may cause two linear movements to occur. First, the second threaded body 42 may move linearly relative to the third threaded body 44, or vice-versa. Second, the first threaded body 40 may move linearly relative to the second threaded body 42. In the instant embodiments, since the body brace 14 is engaging the patient or user's body and therefore is fixed in position, the rotation of grab 54 results in the movement of threaded body 42 and movement of threaded body 40 toward or away from the body brace 14.

Figure 9:
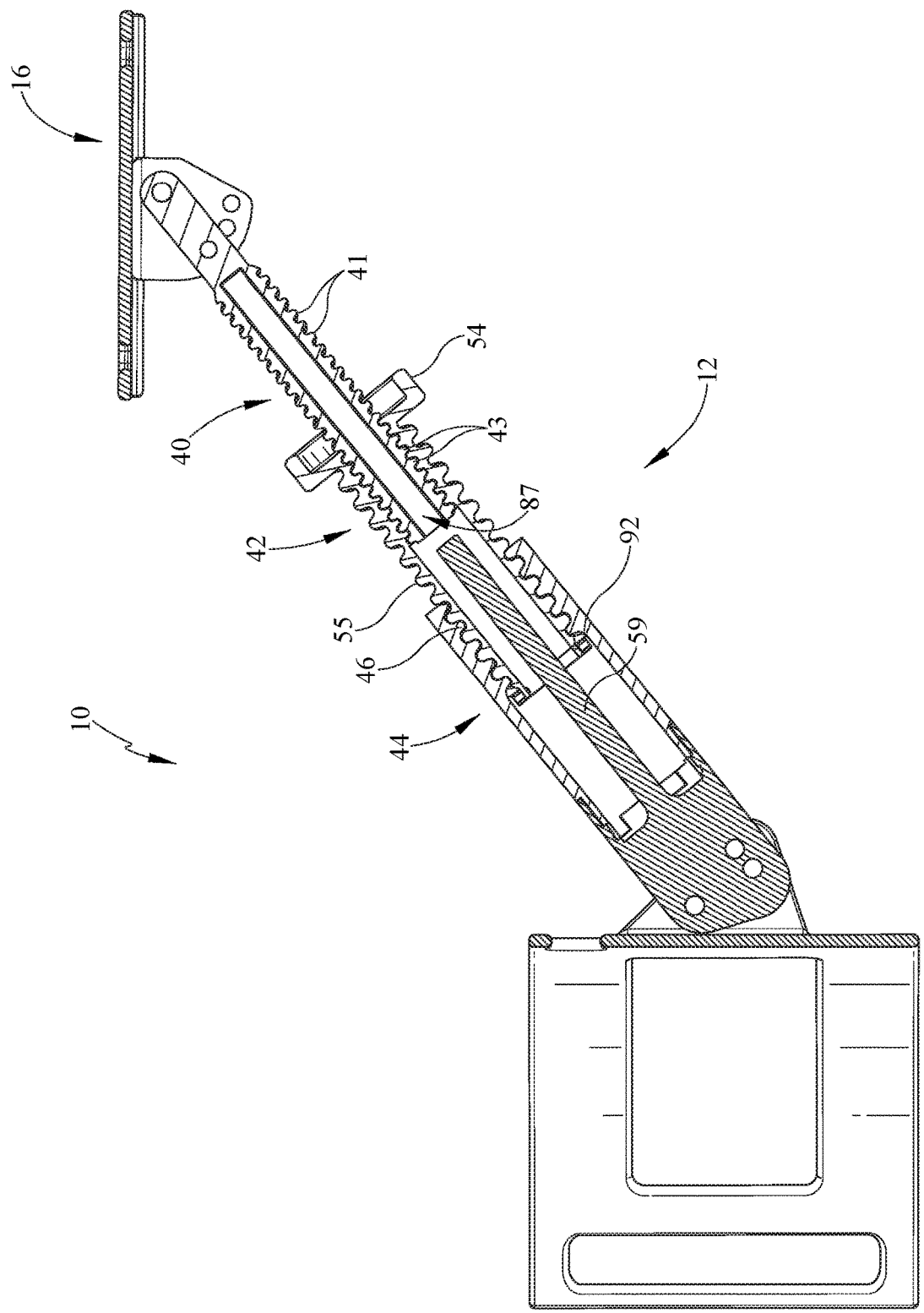
FIG. 9 is a section view of the actuator in a second more extended position; and, FIG. 10 is an alternate embodiment which provides additional length to the actuator for additional range of motion.

With regard to FIG. 9, a section view of the brace 10 is shown with the actuator 12 shown in a position extended from that shown in FIG. 8. In the instant figure, the first threaded body 40 is shown extending from the second threaded body 42. At a lower end of the second threaded body 42, the threaded body 42 may include a rib, protuberance or other structure defining a stop 92 to inhibit removal of the second threaded body 42 from the third body 44. Once the rotation of the second threaded body 42 is stopped, the first threaded body 40 may also no longer move. Thus a second additional stop may be used but is not necessary.

Additionally, in this view, the actuator 12 is extended in such a manner that the anti-rotation rod 59 is disengaged from the first threaded body 40. As shown, the rod 59 is removed from the end of the first threaded body 40 and the aperture 87 therein which receives the rod 59. The anti-rotation rod 59 may also be formed with a length so not to disengage the first threaded body.

Figure 10:
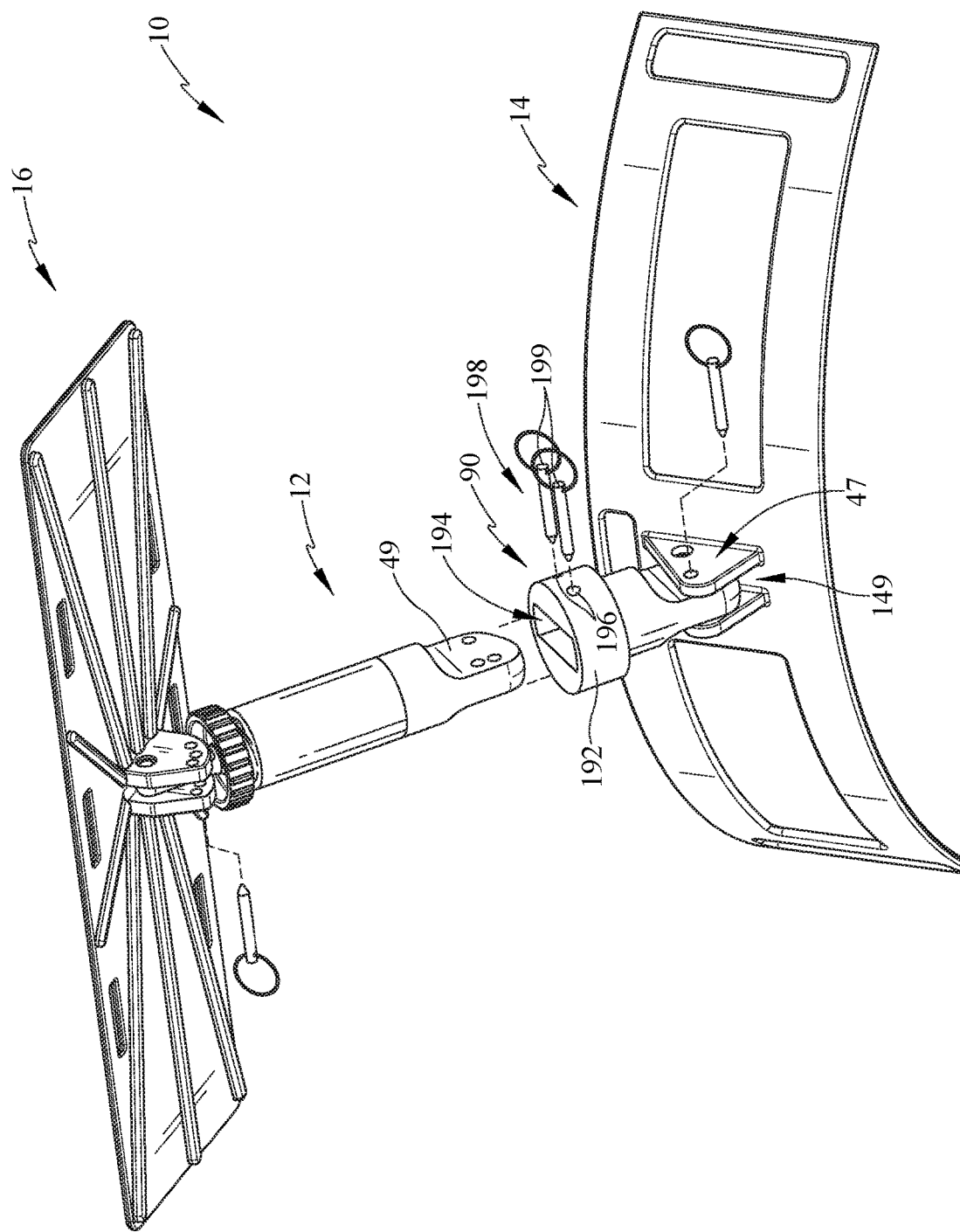

Referring additionally to FIG. 10, a further embodiment is provided to increase the range of motion of the user's shoulder. The actuator 12 may further comprise an extension 90 which provides a longer length for the actuator 12. This allows a patient to increase abduction movement of the arm and shoulder being treated. The extension 90 may have any of various axial lengths which provides the desired abduction Various types of extension devices may be utilized. According to some embodiments, the extension 90 has a collar 192 which includes a slot 194. The tang 49 may be received in the slot 194 of the collar 192. Additionally, the collar 192 may comprise one or more apertures 196 which receive one or more fasteners 198. In the instant example, the fasteners 198 may be pins 199 similar to the fasteners previously shown and described. The fasteners 198 may extend through the collar 192 and into the apertures in the tang 49. Once this is done, the actuator 12 is connected to the extension 90. One skilled in the art should realize that other embodiments for connection may be provided.

At the opposite end of the extension 90 is a tang 149, which cooperates with the clevis 47. Once the extension 90 is connected to the clevis 47, the angle of the extension 90 and actuator 12 may be adjusted relative to the body brace 14. With this adjustment made, the actuator 12 may be adjusted in an axial direction to the desired position to achieve the desired positioning of the shoulder and arm of the patient P (FIG. 1). Further, while one embodiment is shown, is should be understood that an embodiment is provided but other embodiments of the extension may be provided in order to increase the range of motion of the patient using the brace 10.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the invent of embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases.

Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding,"

"composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

The foregoing description of methods and embodiments has been presented for purposes of illustration. It is not intended to be exhaustive or to limit the invention to the precise steps and/or forms disclosed, and obviously many modifications and variations are possible in light of the above teaching. It is intended that the scope of the invention and all equivalents be defined by the claims appended hereto.

The invention claimed is:

1. An orthopedic brace, comprising:
a body brace and an arm platform;
an actuator which is movable to extend and retract the arm platform relative to the body brace;
said actuator comprising a first threaded body, a second threaded body and a third threaded body;
a first end of said actuator having a connector which engages said arm platform, said connector providing angular adjustment of said actuator relative to said arm platform;
a second end of said actuator having a second connector which engages said body brace;
said first threaded body having a thread in a first direction;
said second threaded body having a first thread in said first direction and a second thread in a second opposite direction.

2. The orthopedic brace of claim 1, said third threaded body having a third thread in said second opposite direction.

3. The orthopedic brace of claim 1, further comprising an extension which may be connected to said actuator.

4. An orthopedic brace, comprising:
a body brace and an arm platform;
an actuator which is movable to extend and retract the arm platform relative to the body brace;
said actuator comprising a first threaded body, a second threaded body and a third threaded body;
a first end of said actuator having a connector which engages said arm platform, said connector providing angular adjustment of said actuator relative to said arm platform;
a second end of said actuator having a second connector which engages said body brace;
an internal anti-rotation guide rod extending longitudinally from one side of said actuator to a second side to inhibit rotation of said first and third threaded bodies.

5. The orthopedic brace of claim 4, said second connector providing angular adjustment of said actuator relative to said body brace.

6. An actuator of an orthopedic brace, comprising:
a first body which extends and retracts relative to a second body, said first body having a thread in a first direction;
said second body having a first thread in said first direction and a second thread in a second opposite direction;
a third body which extends and retracts relative to said second body;
a body brace at one end of said actuator;
an arm platform at a second end of said actuator;
at least one of said body brace or said arm platform being angularly adjustable relative to said actuator.

7. The actuator of claim 6, further comprising an extension to lengthen said actuator.

* * * * *